United States Patent [19]

Pless et al.

[11] Patent Number: 4,640,298
[45] Date of Patent: Feb. 3, 1987

[54] ESOPHAGEAL ELECTRODE PROBE USEFUL FOR ELECTRICAL STIMULATION OF THE HEART

[76] Inventors: Peter Pless, Åsumvej 460, 5240 Odense NØ; Henning R. Andersen, Fruens Bøge Alle 4, 5250 Odense SV, both of Denmark

[21] Appl. No.: 759,930

[22] Filed: Jul. 29, 1985

Related U.S. Application Data

[63] Continuation of Ser. No. 671,023, Nov. 14, 1984, abandoned, which is a continuation of Ser. No. 517,395, Jul. 26, 1983, abandoned, which is a continuation of Ser. No. 321,173, Nov. 12, 1981, abandoned.

[30] Foreign Application Priority Data

Jun. 3, 1980 [DK] Denmark .............................. 2380/80

[51] Int. Cl.$^4$ ............................................. A61N 1/04
[52] U.S. Cl. ................................ 128/784; 128/419 D; 128/419 P
[58] Field of Search ........................ 128/207, 15, 419 P, 128/419 PG, 419 D, 670, 696, 784–786

[56] References Cited

U.S. PATENT DOCUMENTS

| | | | |
|---|---|---|---|
| 3,326,207 | 6/1967 | Egan .................................. | 128/698 |
| 3,561,430 | 2/1971 | Filler, Jr. et al. .................... | 128/661 |
| 4,088,138 | 5/1978 | Diack et al. ......................... | 128/721 |
| 4,090,518 | 5/1978 | Elam ................................. | 128/207.15 |
| 4,304,239 | 12/1981 | Perlin ................................ | 128/670 |

FOREIGN PATENT DOCUMENTS 0121090  9/1971  Denmark .
0133400  1/1979  Fed. Rep. of Germany ...... 128/786

OTHER PUBLICATIONS

Sandoe et al., *Klinisk Elektrokardiografi, Arytmidiagnostic og-Behandling*, FADL's Forlag, Copenhagen, 1978, pp. 44–6 and 190–191.
Andersen et al., "Trans Esophageal Pacing", *Pace*, vol. 6, pp. 674–679, Jul.–Aug. 1983.

*Primary Examiner*—William E. Kamm
*Assistant Examiner*—Mitchell J. Shein
*Attorney, Agent, or Firm*—Finnegan, Henderson, Farabow, Garrett & Dunner

[57] ABSTRACT

An electrode probe (1), in particular for electrical stimulation of the heart from the interior of the esophagus, is constructed on the basis of the new finding that the distance from the transition between the stomach and the esophagus to the transition between the left atrium and the left ventricle is substantially the same in adults. The electrode probe (1) has a maximum of two stimulation zones (A, B) (one for atrium and ventricle, respectively) which, when fitted on expansible parts of the probe, allows heart stimulation to be performed with simple equipment without expert assistance, when the distance between a means (4X) for fixing the axial position of the probe in the esophagus and the stimulation zones (A, B) are determined in accordance with the above finding, so that in all conditions optimum stimulation of the heart and reduction in the required stimulation voltage are obtained.

3 Claims, 7 Drawing Figures

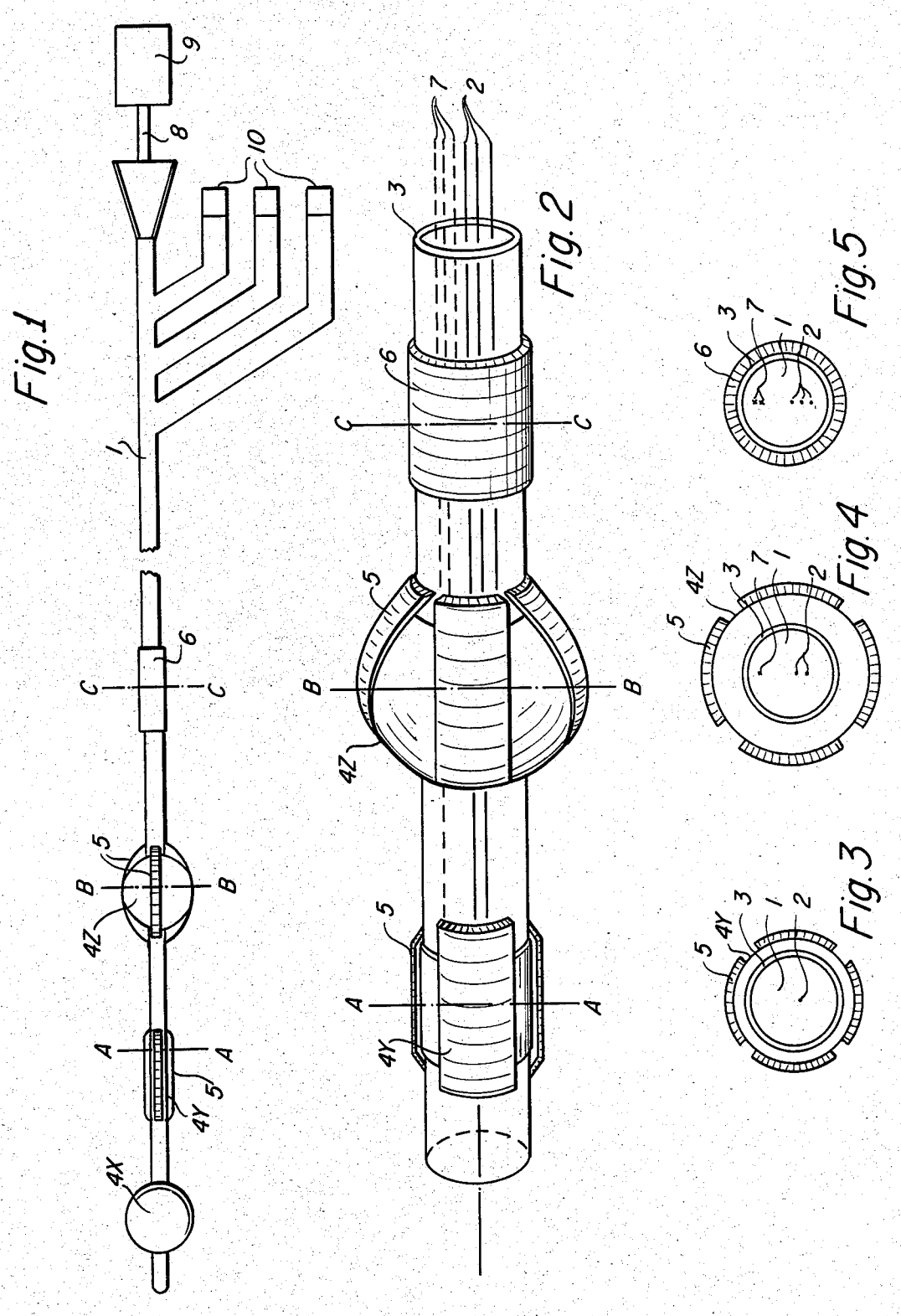

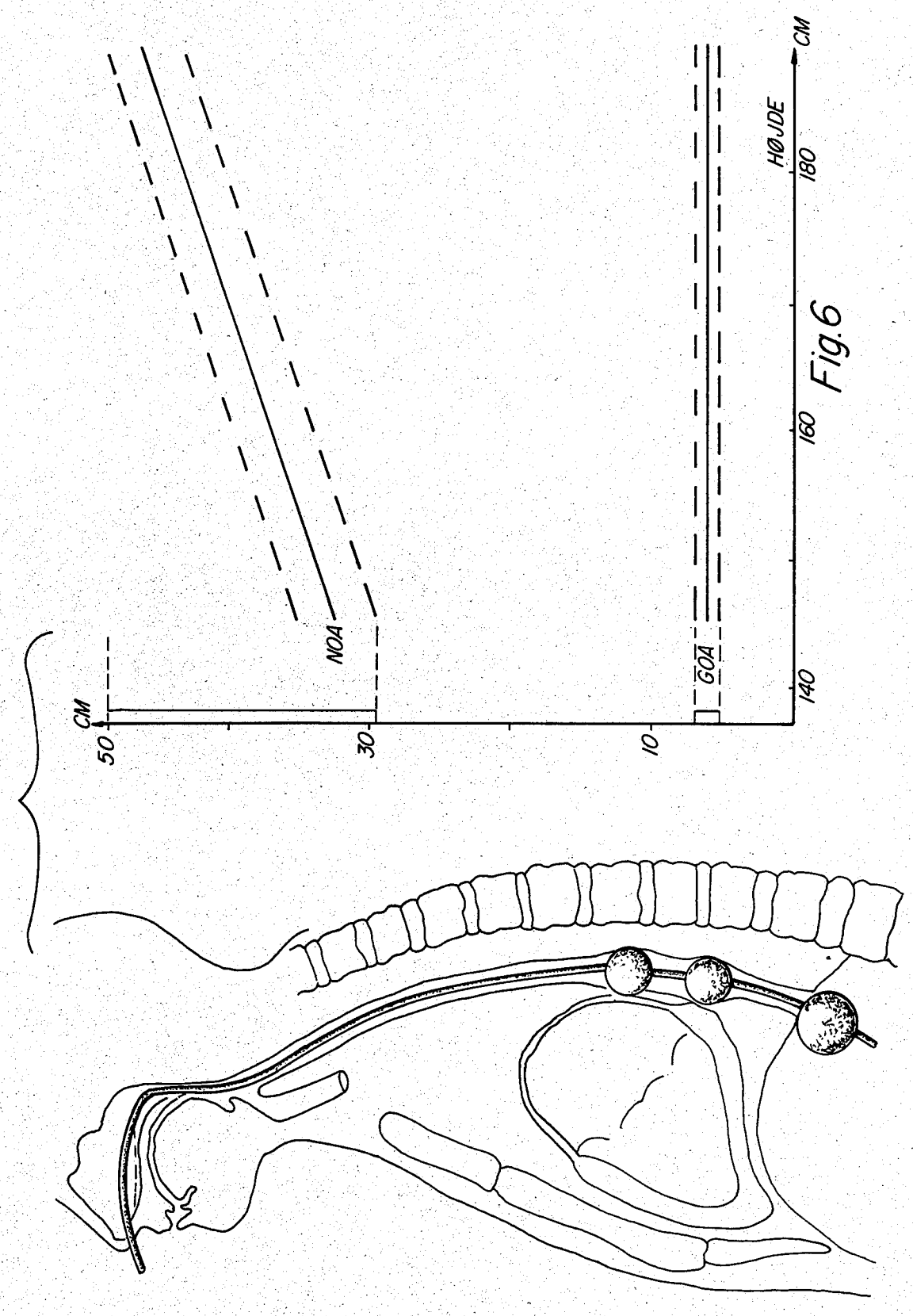

ESOPHAGEAL ELECTRODE PROBE USEFUL FOR ELECTRICAL STIMULATION OF THE HEART

This application is a continuation of Ser. No. 671,023, filed Nov. 14, 1984, now abandoned, which is a continuation of Ser. No. 517,395, filed July 26, 1983, now abandoned, which is a continuation of Ser. No. 321,173, filed Nov. 12, 1981, now abandoned.

The invention relates to an electrode probe of the type defined in the introductory portion of claim 1, said probe being particularly useful for electrical stimulation of the heart from the interior of the esophagus.

Electrical stimulation of the heart (pacing) over an extended period of time is usually performed by inserting transvenous catheters into the right atrium and the right ventricle. The technique has been developed and improved so that today this treatment can be effected with very great safety at wards where adequate technical equipment and the necessary expertise are available.

Sometimes, however, emergency (bed side) pacing is needed for patients with a sudden instance of heart failure, and pacing of them during the transport to specialist wards where a temporary or permanent transvenous pace catheter can be implanted.

Essential indications for emergency pacing are the following ones:
1. heart arrest (asystole)
2. sudden instance of fatal AV-block
3. sudden instance of symptom-giving bradycardia
4. block-bradycardia caused ventricular tachycardia
5. Wolff-Parkinson-White tachycardia
6. as a "safety net" in cases of severe tachycardia
7. as a "safety net" in operations on patients suffering from bradycardia.

If emergency (bed side) pacing is to be of practical use, i.a. the following requirements should be met:
1. the pacing must admit of being performed rapidly
2. the pacing must be simple to perform with relatively simple means
3. the pacing must give a sufficient stimulation without serious side effects
4. the pacing must admit of being performed with great safety.

The present known methods of emergency pacing are the following ones, the disadvantages being stated for each method:
1. External pacing with conventional defibrillator
   (a) this method requires great current intensity
   (b) the method causes burn
   (c) the method is extremely painful to the patient.
2. Perthoracic pacing with implanted myocardial electrode
   (a) is an invasive surgical intervention
   (b) cannot be performed sufficiently rapidly
   (c) is too complicated in an emergency situation.
3. Transvenous pacing
   (a) is an invasive surgical intervention
   (b) insertion of the electrode is uncertain without simultaneous radioscopy
   (c) danger of perforation of vein, atrium or ventricle.
4. Transthoracic pacing with needle electrode
   (a) is an invasive surgical intervention
   (b) placing of the electrode is attended with uncertainty
   (c) may lead to bleeding/hemopericardium
   (d) may cause pneumothorax
   (e) may cause puncture of artery or vein.

An example of a catheter for transthoracic pacing is the catheter constructed by Shinnick et al. (U.S. Pat. No. 3,680,544).

This instrument is intended to be inserted through the front of the chest wall, perforating all anatomic structures located between the heart cavity and the skin.

The catheter is retained in the heart cavity by an end-positioned fixing mechanism, and the stimulation electrodes are placed at a distance from this mechanism such that they are embedded in the heart muscle. The catheter is also provided with a system of valves, which are i.a. to prevent backflow of blood as the intervention is invasive.

5. Transesophageal pacing with various types of pace catheters

This is a relatively disregarded and insufficiently developed method of emergency pacing. In the early studies, use was made of electrodes of the types normally employed for transvenous pacing or for EKG recording from the esophagus, either with a unipolar electrode inserted into the esophagus and an inert electrode fitted precordially, or with bipolar electrodes where also the inert electrode was placed in the esophagus.

These experiments required great current intensity and/or potential differences (40–250 V), and the effect was uncertain, one reason being uncertain placing of the electrode with respect to the part of the heart (left atrium or ventricle) to be stimulated.

An improvement of the transesophageal pacing was obtained by placing the electrode on an inflatable and deflatable balloon. Thus, Mitsui et al. (1973) Cardiac Pacing, p. 282 ff., Editor: Thalen. van Gorcum, Assen, The Netherlands, reports successful experiments on two adults, who were stimulated with a bipolar metal tip electrode applied to a balloon, which was inserted in a deflated state through the nostril and inflated at a suitable distance from the wing of the nose. According to Mitsui this distance varies from 35 to 45 cm (in Japanese), and an EKG must therefore be taken during and after the insertion, and the placing must be determined on the basis of the maximum amplitude (for the QRS complex in case of ventricular pacing and for the P-top in case of atrial pacing). This requires availability of EKG equipment and complicates and delays emergency pacing. Moreover, the results are not reproducible in all cases, and the potential differences (20 to 30 V) are undesirably great.

Meisner et al. (1977) Cardiac Pacing, Editor: Watanabe (Excerpta Medica) describes a unipolar electrode with an electrically conductive, flexible plastic band fixed over a balloon, while the inert electrode is applied precordially. Meisner's experiments were made on newborn babies, infants and small children whose build make them difficult to treat by the above-mentioned alternative methods. Meisner, too, determined the correct electrode localization by simultaneous recording of EKG.

Meisner succeeded in pacing the heart of all his 19 patients at voltages betwen 6 and 15 V, but it is uncertain whether the reduction of these voltages over Mitsui's 20 to 30 V is solely due to the fact that his patients were children.

Also a recent report by Kerr et al., PACE, vol. 4, March-April 1981, describes pacing of patients suffering from a WPW syndrome with a bipolar electrode after EKG recording, necessitated by the variable distance from nares to the AV transition (38.3 to 44.9 cm).

Conclusively, it may be said that none of the previous balloon electrodes provides certainty of correct placing of the pace electrode, and that this placing is sought optimized by simultaneous EKG recording. This uncertainty is primarily caused by the placing being determined on the basis of the distance from the nose wing to the heart, which, as stated by the authors, varies considerably from individual to individual, particularly as a function of the height.

Nor have the known types of electrodes adequately met the requirement for close contact between the electrode and the posterior face of the heart. The prior art approaches therefore had to rely on great current intensity and potential differences.

However, a quite decisive deficiency is that the types of electrodes whose positions are determined by simultaneous EKG recording cannot with safety be placed in fatal cardiac arrest cases (asystole), where the heart does not emit electrical impulses. This is the more serious because the experts agree that pacing is the most effective treatment, and that chemical agents, such as adrenalin or isoprenaline, are not sufficiently effective, cf. Sandøe and Sigurd "Klinisk elektrocardiografi, arytmidiagnostik og-behandling", FADL's Forlag, Copenhagen 1978, p. 190–91, and Sandøe et al., "Intensiv observation og behandling af patienter med akutte hjertesygdomme", FADL's Forlag, Copenhagen, 2nd edition, 2nd volume 1976, p. 268–69.

Another known type of electrode to be applied in the esophagus is the diagnostic EKG electrode probe constructed by Erik Ole Jørgensen (Danish Pat. No. 121 090), but this probe is not intended or proposed for use as a stimulation probe.

This probe has an end-positioned inflatable balloon for insertion into and inflation in the stomach as well as a plurality, expediently 15 to 20, of annular metal electrodes. The electrodes are placed in a predetermined spaced relationship so that a reproducible EKG can be taken from the same patient at different moments. In the construction of this electrode probe no regard has been paid to the placing of the electrodes with respect to given anatomic structures in the posterior face of the heart.

The object of the invention is to provide an electrode probe which permits effective emergency transesophageal pacing under all the indications mentioned in the foregoing, including asystole, and which is not vitiated by the above-mentioned drawback as regards uncertainty of placing, so that it will also be possible to work with lower current intensity and potential differences.

A particular object of the invention is to provide an electrode probe which can be placed in an optimum position with respect to the part of the heart which is relevant to the pacing, without simultaneous recording of EKG, to thereby provide for emergency pacing out of specialist wards, e.g. during the transport to a hospital.

On the other hand, the object is also to provide a probe of a construction that renders it useful, without modifications, in connection with EKG recordings, so that it can be used at hospital wards having EKG equipment and thereby allow transesophageal EKG recording if desired, e.g. during periods where the patient is not considered to need stimulation, without it being necessary to remove the probe and insert a new EKG electrode.

These objects are obtained with the electrode probe of the invention which comprises a fixing means for axial positioning of the probe with respect to the stomach and comprises a plurality of stimulation electrodes to provide an electrical field with respect to an inert electrode, and which is characterized by the provision of a maximum of two stimulation zones on the probe in the form of electrode means applied to an expansible part of the electrode probe, so that each electrode means defines at least one electrode which in the expanded state of the probe is positioned at a distance from the fixing means, said distance being predetermined on the basis of anatomic conditions.

The invention is based on the surprising finding that while the distance from the wing of the nose to the heart, as measured through the esophagus, varies, as stated, from individual to individual, the distance from the transition between stomach and esophagus to the transition between left atrium and left ventricle is for practical purposes independent of the height of adults.

This finding is at variance with previous expert opinion, cf. e.g. Sandøe and Sigurd, op. cit., p. 44, where in connection with a discussion of the EKG electrode probe of Danish Pat No. 121 090 it is said about three electrodes in fixed spaced relationship with the balloon that "their positions with respect to atrium of course vary with the size and build of the individual".

FIG. 6 shows the linear regression line with standard deviation of the distance outlined in the figure, where NOA represents the distance from the wing of the nose (nares) to the transition between atrium and ventricle, while GOA represents the distance from the transition between stomach and esophagus (cardia ventriculi) and the transition between atrium and ventricle, which was not known before but was measured in 1980 by the inventors in the specific population of varying height. It is readily apparent from the figure that, as previously argued, there are great individual differences in the NOA distance. This variation also applies to individuals of the same height owing to differences in their builds. Thus, it is understandable that the previous experiments with transesophageal pacing have been performed with varying success because the place of the electrodes was not well-defined.

Likewise, it appears that the GOA distance is essentially independent of the height of the individual.

Based on this finding, the inventors have realized that by providing two stimulation zones, in the form of electrode means each defining at least one electrode, on an electrode probe of the type having at its distal end a fixing means for application in the stomach, an effective pacing can be obtained, provided that the place of the electrodes have been determined in accordance with the anatomic conditions mentioned in the foregoing.

The desired close contact with the posterior side of the heart is provided for by fitting the electrode means on an expansible part of the probe. In a preferred embodiment, the two electrode means are fitted on their respective expansible parts of the probe, e.g. on two balloons, while the inert electrode, with respect to which an electrical field is established during the stimulation, is placed on a non-expansible part of the probe. Each balloon then has a separate air passage to cause the expansion.

In this embodiment, the inconvenience caused to the patient by the expansion is minimized, and the probe can be placed rapidly.

In an alternative embodiment both electrode means are applied to the same expansible member. This facilitates the expansion as one air passage is sufficient, but may add to the inconvenience to the patient owing to the increased length of the expanded area.

In principle, there is nothing to prevent the inert electrode from being mounted on the expansible member too. However, this necessitates further elongation and will therefore increase the inconvenience to the patient.

Finally, the inert electrode does not have to be fitted on the probe itself, but may be applied precordially. According to circumstances, this may provide improved certainty of the setting-up of the optimum electrical field through the heart, but the placing of the probe and the electrode before implementation of the pacing is more time-consuming.

Further modifications and details of the probe of the invention will be described after the discussion of the drawing, which schematically shows a preferred embodiment of the probe as defined in claims 2 and 3, as well as details of this embodiment. The invention is not restricted to this, as will appear from the following.

FIG. 1 shows a stimulation probe according to the invention,

FIG. 2 shows a detail of the stimulation probe shown in FIG. 1,

Figure 7:
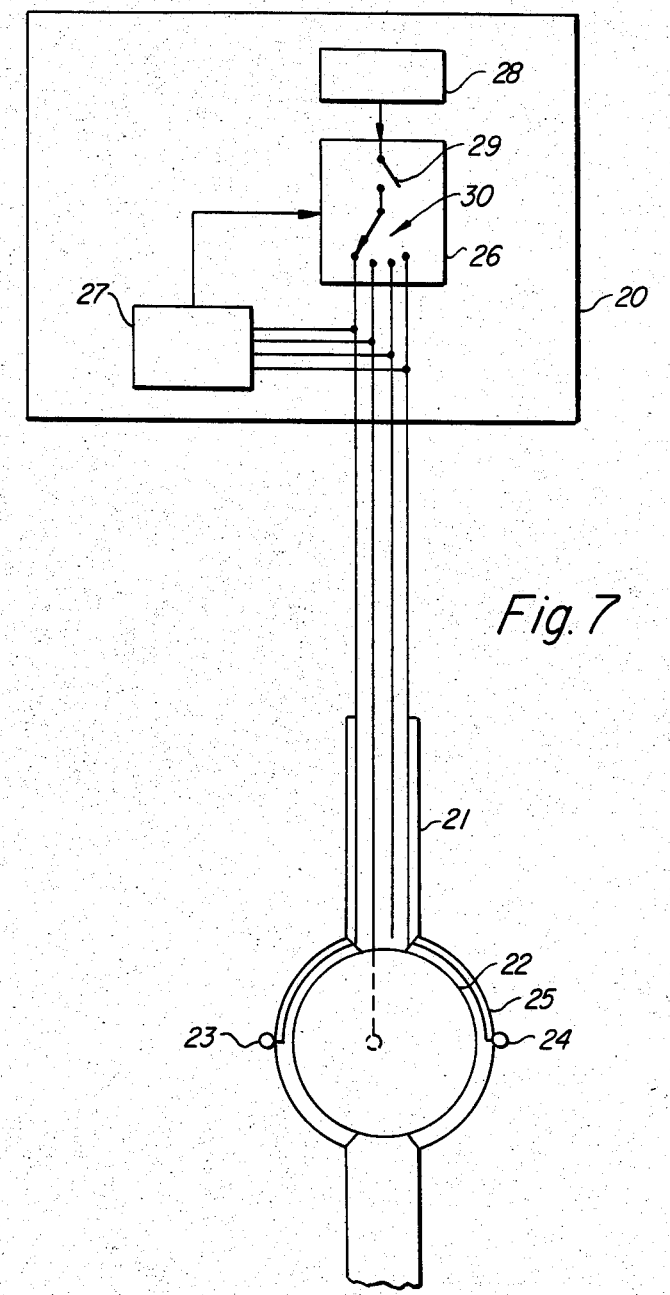

FIGS. 3, 4, and 5 show sections A—A, B—B and C—C taken along the lines A—A, B—B and C—C in FIGS. 1 and 2, and FIG. 6 shows the previously mentioned NOA and GOA distances as a function of the height of the individual, FIG. 7 shows a further embodiment of a stimulation zone on the electrode probe, and a basic circuit diagram for an electrical circuit for the probe.

The stimulation probe consists of a central tube (1) whose upper end has three connections (10) for mutually independent supply of air through three air passages (2). An insulating sheath (3), which may expediently be of a polymeric material, is cast around the central tube. Three balloons (4X, 4Y, and 4Z) are attached to the sheath (3) at the end of the mutually independent air passages (2). The lower balloon (4X) serves as a fixing means. The other two balloons (4Y and 4Z) are provided with electrode means comprising resilient, electrically conductive materials (5) fitted in rectangular bands longitudinally of the probe and attached to the sheath (3). In the upper end of the probe, a cylindrical, inert electrode (6) is attached to the sheath (3).

All the electrodes A, B, and C are connected to leads (7), which spaced apart have been run and are fixed to the electrode material (5). As shown in FIG. 1, the leads may be gathered in a common cable (8) and be run to a schematically shown multi-outlet (9).

FIG. 2 shows the two electrode balloons 4Y and 4Z in a deflated and inflated state, respectively. FIG. 3 shows a section A—A through the deflated electrode balloon 4Y, and FIG. 4 shows a section B—B through the inflated electrode balloon 4Z. FIG. 5 shows a section C—C through an inert electrode (6); the same reference numerals are used in FIGS. 3-5 as in FIGS. 1 and 2.

With reference to the figures, the following may be said about the dimensions of the probe:

The diameter of the probe is determined by the wish for minimizing the inconvenience to the patient while providing accommodation for the internal air passages and leads. A suitable diameter is 4 to 6 mm, corresponding to the diameter of the esophagus in a relaxed state.

The balloons 4Y and 4Z are to be inflated to ensure good electrode contact with the posterior wall of the heart. This is usually provided for by inflation to a diameter of 2 or 3 cm.

The balloon 4X serves as a fixing means for axial positioning of the probe with the respect to the stomach so that the stimulation zones with certainty get the positions realized as advantageous in accordance with the foregoing, and must be inflated to avoid retraction through the upper orifice of the stomach. This normally requires inflation to at least 3 cm, preferably 5 or 6 cm.

As explained above, the invention is based on the determination of the distance between the fixing means (the balloon) 4X and the stimulation zones (the balloons) 4X and 4Z on the basis of anatomic conditions, and these distances have been found to approximately constant for a given population of adults.

For Danes, the following distances are expedient:

Distance from the transition between the fixing means (balloon 4X) and the probe to the centre of the lower stimulation zone (balloon 4Y): about 4 cm.

Distance from the transition between the fixing means (balloon 4X) and the probe to the centre of the upper stimulation zone (balloon 4Z): about 9 cm.

It is believed that these distances also hold for other countries, but it cannot be excluded that there are minor ethnically determined differences, which can easily be examined by autopsy and/or esophagus EKG.

It is also believed that relevant anatomic relations can be found later which allow adaptation of the probe so that it becomes useful for babies and infants as well.

In the embodiment where the inert electrode (6) is placed on the probe, the distance of it to the centre of the upper stimulation zone (balloon 4Z) is expediently about 10 cm.

In connection with the figures, the stimulation zones are illustrated by expansible balloons (4Y and 4Z), which are inflated by means of air. Alternatively, they can be composed of a porous material, such as foam rubber or another foam that can be kept deflated by means of a vacuum and be inflated by release of the vacuum.

As explained above, the stimulation zones 4Y and 4Z can also be formed by one elongate, expansible member that may be arranged analogously. This member may also be extended to comprise the inert electrode (6).

In the figures the electrode means are illustrated as four electrically conductive bands. These bands may be partly covered, as a greater field strength and a more concentrated field can be obtained by reducing the electrode area, which permits the current intensity to be reduced. Previous electrodes had an area of 100 to 200 $mm^2$, but it is believed that the total electrode area in the probe of the invention can be reduced, e.g. to about 20 $mm^2$ or even down to about 3 to 5 $mm^2$ per electrode.

The invention is not restricted to probes having four electrodes, and any expedient number may be provided, as determined by experiments. To obtain an additional decrease in the electrode area, 6 or 8 seems to be suitable.

FIG. 7 shows an additional embodiment of a stimulation zone on the electrode probe and a basic circuit diagram for an electrical circuit (20) for the probe. It will be appreciated that a circuit (20) is provided for each stimulation zone, or that the circuit (20) may comprise change-over switch means for switching between the stimulation zones.

In FIG. 7 an expansible part of the probe (21) comprises an inner balloon (22) which can be inflated by means of air through a not shown tube in the probe (21). The shown embodiment includes four electrodes, such as the electrodes (23, 24) which are spherical, e.g. by casting a gold alloy on the end of a lead. The respective leads are, as shown in the figure, run to the circuit (20) through the electrode probe, and the leads are fitted on the exterior thereof to avoid perforating the balloon (22). An additional balloon (25) is provided to protect the leads and to retain the electrodes along a great circle for the balloon (22).

As explained above, a lead is run to the circuit (20) for each electrode, and each electrode is connected partly to a switching circuit (26), partly to an amplitude discriminator circuit (27), which may also comprise a timing circuit. The circuit (20) also comprises a generator (28) to generate electrical stimulation impulses. The timing circuit is designed so that in the periods between the stimulation impulses the circuit (27) can receive EKG signals from each of the electrodes in the probe, e.g. by actuation of the contact (29). The circuit (27) is designed to detect, in a known manner, the most powerful one of the EKG signals and to determine from which electrode the most powerful signal has been received. Then control signals are applied from the circuit (27) to the circuit (26) so that the contact (29) is closed and a change-over switch (30) is caused to assume a position such that the stimulation signals from the generator (28) are applied to the very electrode that receive the most powerful EKG signal. The advantage of this is that the electrical stimulation of the heart is automatically caused by the electrode which has the best electrical contact with the heart, and the necessary stimulation voltage can thus be reduced.

In the use of this embodiment in case of asystole where the heart emits no EKG recordable impulses, stimulation signals will be applied by all the electrodes until the heart begins beating again and EKG signals can be recorded. Then the three electrodes emitting the weakest signals will be disconnected in accordance with the above explanation.

The discrimination between the present electrodes is explained in the foregoing in connection with the recorded amplitudes of EKG signals. This discrimination can of course also be performed on the basis of other parameters, e.g. the difference in time between the recorded signals from the electrodes.

The advantages of the probe of the invention have been explained in the foregoing essentially in connection with the presence of two stimulation zones as this provides the greatest flexibility in the application of the probe.

On the other hand, it will often be evident to the responsible doctor what part of the heart is to be stimulated. This applies e.g. in cases of acute heart attacks, corresponding to a plurality of the abovementioned indications for emergency pacing. In that case he will always stimulate the left ventricle owing to missing electrical connection between the atrium and the atrium and the ventricle, and a stimulation of the atrium will have no effect or will even be harmful to the patient. For this reason, it may be desirable to have probes which are only formed with one (lower) stimulation zone in order to minimize the risk of operating errors.

Similarly, e.g. in diagnostic examination of various conductions disturbances between atrium and ventricle, it may be desirable to have probes with only an upper stimulation zone.

The most expedient stimulation time depends especially on the distance between the electrode and the excitable heart tissue as well as the electrode area, cf. M. Schaldach & S. Furman, "Advances in pacemaker technology", Springer, New York, 1975. A suitable time for the embodiment of FIG. 7 seems to be 10 milliseconds, but shorter periods of stimulation such as the usual 2 milliseconds or so used in traditional transvenous pacing may also be employed.

The expedient pulse rate varies with the indication on which the pacing is based. Usually, a rate corresponding to the normal heart rate, i.e. 60 to 70 impulses/min., is used, but significantly higher rates, e.g. up to 400 impulses/min. may be used for purposes of treatment as well as diagnostics.

We claim:

1. An electrode probe adapted to be inserted into the esophagus of a patient and to provide stimulation of the heart which comprises a central tube provided with radially expansible fixing means at its distal end for axial positioning of the probe with respect to the stomach, a maximum of two stimulation zones selected from a first stimulation zone being positioned on a radially expansible part of the probe at a first distance of about 9 cm from the fixing means and a second stimulation zone being positioned on a radially expansible part of the probe at a second distance of about 4 cm from the fixing means, said first and second distances being predetermined on the basis of the distance from the transition between stomach and esophagus to the transition between the left atrium and the left ventricle so as to ensure that each of the first and second stimulation zones upon expansion of the expansible parts is in close contact with the posterior side of the left atrium or ventricle respectively, and an inert electrode being positioned with respect to said stimulation zones as to provide an electrical field through the heart.

2. An electrode probe according to claim 1, wherein two stimulation zones are fitted on their respective expansible parts of the probe, the inert electrode being fitted on a non-expansible part of the probe closer to its proximal end.

3. An electrode probe according to claim 2, wherein separate air passages are provided in the central tube for expanding the expansible parts and the fixing means respectively.

* * * * *

UNITED STATES PATENT AND TRADEMARK OFFICE
CERTIFICATE OF CORRECTION

PATENT NO. : 4,640,298

DATED : February 3, 1987

INVENTOR(S) : PETER PLESS ET AL.

It is certified that error appears in the above-identified patent and that said Letters Patent is hereby corrected as shown below:

After Foreign Application Priority Data, insert

--June 3, 1981 PCT PCT/DK81/00061--.

Signed and Sealed this

Thirteenth Day of October, 1987

Attest:

DONALD J. QUIGG

*Attesting Officer*  *Commissioner of Patents and Trademarks*